US00PP11986P2

(12) United States Plant Patent
Lamb et al.

(10) Patent No.: US PP11,986 P2
(45) Date of Patent: Jul. 10, 2001

(54) SPATHIPHYLLUM PLANT NAMED 'CONNIE'

(75) Inventors: Ann E. Lamb, Sebring; David R. Lilly, Boynton Beach, both of FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 0 days.

(21) Appl. No.: 09/238,730

(22) Filed: Jan. 28, 1999

(51) Int. Cl.[7] ..... A01H 5/00

(52) U.S. Cl. ..... Plt./364

(58) Field of Search ..... Plt./364

*Primary Examiner*—Bruce R. Campell
*Assistant Examiner*—Kent L. Bell
(74) *Attorney, Agent, or Firm*—Foley & Lardner

(57) ABSTRACT

A Spathiphyllum plant named 'Connie' characterized by its intermediate stature, highly branched growth, shiny, textured foliage, and oblong white spathes. Plants of 'Connie' grow very quickly to marketable size, bloom and re-bloom quickly, and are adaptable to a variety of pot sizes from 15-cm through 25-cm. Plants of 'Connie' are well adapted to indoor conditions.

1 Drawing Sheet

The present invention comprises a new and distinct cultivar of Spathiphyllum botanically known as *Spathiphyllum hybrid*, and referred to by the cultivar name 'Connie'.

The new cultivar is the product of a breeding program carried out by the inventors Ann E. Lamb and David R. Lilly. The new cultivar named 'Connie' is the result of a cross made in Apopka, Fla. in November of 1993. The female parent was Spathiphyllum 'Petite' (unpatented) and the male parent was a selection of Spathiphyllum Mauna Loa 'Linda' (unpatented) selected and maintained by the inventors, and used only for breeding purposes.

Spathiphyllum 'Petite' is a small plant, grown in 4"–6" pots. Spathiphyllum 'Linda' is a large, upright growing variety used in 10"–14" pots, with broad dark green leaves and large bright white spathes held above the foliage. Spathiphyllum 'Connie' is intermediate in growth habit between 'Petite' and 'Linda'. Its leaves are intermediate in size and width between 'Petite' and 'Linda'. The leaves of 'Connie' are considerably more textured than those of 'Petite'. Most notably, plants of 'Connie' are more floriferous than either parent.

The new cultivar named 'Connie' was discovered and selected by the inventors from a group of seedlings of the stated cross in Homestead, Fla. on Feb. 26, 1996. The cultivar 'Connie' was first asexually propagated on Feb. 26, 1996. Propagation by tissue culture in Sebring, Fla., under the supervision of the inventors, was used to increase the number of plants for evaluation and has demonstrated the stability of the combination of characteristics as herein described from generation to generation. To date, at least 5000 plants of 'Connie' per month have been reproduced vegetatively by tissue culture. The variety is stable genetically, and reproduces true to type. The following observations, measurements and values describe plants grown in Homestead, Fla. under greenhouse conditions which closely approximate those generally used in horticultural practice.

The following traits have been repeatedly observed to be characteristics, which in combination distinguish the new cultivar named 'Connie'.

1. Plants of 'Connie' have an intermediate growth habit and are ideally suited for 15-cm through 25-cm pots.
2. The leaves of 'Connie' are dark-green, shiny, textured, and have a wavy margin.
3. Plants of 'Connie' naturally bloom early, abundantly, repeatedly, and year-round.

4. Plants of 'Connie' are full and very well branched.
5. Plants of 'Connie' grow very quickly and vigorously.
6. Plants of 'Connie' are particularly well adapted to indoor conditions.

The new cultivar named 'Connie' can be compared to the well-known cultivar 'Viscount' (unpatented). 'Connie' is distinguished from 'Viscount' by its highly branched habit, narrower leaves, and more rapid growth. On average, plants of 'Connie' finish to marketable size in 6" pots in about 6 months, to 8" pots in 8 to 9 months, and to 10" pots in 9 to 11 months, as observed in Homestead, Fla. In comparison to 'Viscount', plants of 'Connie' bloom earlier, more abundantly, and year-round. Mature plants of 'Connie' naturally bloom as early as late October or early November whereas mature plants of 'Petite', 'Viscount', and 'Linda' naturally bloom in December or January.

Color references are measured against The Royal Horticultural Society Colour Chart (R.H.S.) except where general terms of ordinary dictionary significance are used. Phenotypic characteristics such as color or plant height may vary depending on climate, horticultural practices such as light level and fertilization rate, among others, without however any variance in genotype.

The photographic illustration depicts a 14-month old plant of Connie in a 25-cm pot initiated from three microcuttings obtained by tissue culture and grown under appropriate growing conditions. Colors are as accurate as possible with a color illustration of this type.

Origin: Seedling selected from cross described above.

Classification: *Spathiphyllum hybrid*, cv. 'Connie'.

Propagation: Asexual reproduction either by tissue culture.

Plant: Under appropriate growing conditions, 'Connie', attains a size of approximately 58 cm to 62 cm in height and approximately 100 cm to 120 cm in width. Height is measured from the soil surface to the top of the leaf canopy. 'Connie' attains a height of approximately 78 cm to 82 cm including the inflorescences (measured form soil surface to apex of spathes).

Branching: A 10" pot initiated from three single shoot microcuttings has approximately 18 branches after 11 months growth in Homestead, Fla.

Leaves:

*Form.*—The leaf blade is ovate with an acuminate apex and a cuneate base. The margins are entire and distinctly wavy. The midrib tends to curve over the length of the leaf. The leaf blade is typically curved downward at the tip. The leaf surface is textured and shiny.

*Size.*—Leaf blades are approximately 27 cm to 33 cm in length and approximately 9.2 cm to 12.5 cm in width.

*Petiole.*—The petiole is approximately 31.0 cm to 41.3 cm in length from the base of the petiole to the base of the leaf blade on the primary shoot. Secondary shoots are smaller depending on the age of the shoot. The petiole is approximately 4 mm in diameter at the junction of the geniculum and petiole sheath. The portion of the petiole below the geniculum is straight.

*Petiole sheath.*—The petiole sheath is approximately 23 cm to 33 cm in length and approximately 8 mm to 12 mm in width at the midpoint. The tip of the petiole sheath is rounded.

*Geniculum.*—The geniculum is approximately 6.1 cm to 7.6 cm in length and approximately 5 mm to 6 mm in diameter. The color is RHS 146 B.

*Veins.*—Veins are sunken, and the leaf blade is convex between veins on the upper surface giving the leaf a textured appearance. The midrib is sunken. Well-defined primary veins radiate out from the midrib over the length of the leaf. There are approximately 14 pairs of primary veins on the leaf.

*Color.*—Upper surface: Considerably darker than but closest to RHS 137 A. Lower surface: RHS 147 B. Midrib, upper surface: Darker than but closest to RHS 137 A. Midrib, lower surface: RHS 146C. Petiole: Much darker and greener than but closest to RHS 147 B. Petiole sheath: Much darker and greener than, but closest to, RHS 147 B.

Roots: Thick white roots with fine laterals. Microcuttings initiated from tissue culture often have one or more roots initiated at the time of harvest (in-vitro) and planting into soil. If no roots are present when planted in soil, a microcutting usually initiates roots within 1 week of planting.

INFLORESCENCE (SPATHE AND SPADIX)

Spathe:

*Immature.*—The spathe is tightly rolled around the spadix and emerges from the petiole sheath. The spathe is approximately fully open when the peduncle is fully elongated.

*Mature.*—Size: The spathe is approximately 11.6 cm to 19.2 cm in length and approximately 6.5 cm to 9.0 cm in width. It is cupped approximately 1.5 to 2.0 cm in depth. Color: Fully open: Adaxial: Pure white, RHS 155 D. Abaxial: Pure white, RHS 155 D. Midrib and apex: Tinged, RHS 145 A. Faded: Upper surface: RHS 155 D streaked with between 145A and 145B. Lower surface: RHS 155 D streaked with between 145A and 145B. Midrib and apex: Between 145A and 145B. Arrangement: The spathe terminates from a straight peduncle and opens vertically above the leaves. Shape: The spathe is ovate with an attenuate to cuneate base and an elongated twisted acuminate apex. Flowering Response: Depending on the season, approximately 8 to 12 inflorescences will be present on plants. Smaller narrower inflorescences may occur on less mature growth. Lastingness of Individual Spathe (on and off the plant): Spathes of 'Connie' begin to change from white to green after about 3 to 4 weeks, becoming almost entirely green after about 6 weeks. Inflorescences (spathes) last about 7 days off the plant. Growth Rate: On average, plants of 'Connie' finish to marketable size in 6" pots in about 6 months, 8" pots in 8 to 9 months, and 10" pots in 9 to 11 months when initiated from a liner as observed in Homestead, Fla. Inflorescence Fragrance: Sweet, moderately fragrant, most noticeable in the morning. Bud: Measurements were taken from buds which had completely emerged from the petiole sheath. The buds are spindle shaped and approximately 8.5 cm to 10 cm in length measured from the apex to the base. The buds are approximately 9 mm to 11 mm in width measured at the widest point. Bud color is RHS 155 A overall, with 145 A and 145 C at the apex.

*Spadix.*—Size: Approximately 4.6 cm in length and approximately 1.2 cm to 1.6 cm in width. Color: When the spathe unrolls, the spadix is between 158 A and 158 B gradually changing to green, between 146 B and 146 C, as the inflorescence fades.

*Peduncle.*—The peduncle is approximately 65 cm to 70 cm in length measured from its base to the base of the spathe, and approximately 4.5 mm in diameter measured at its midpoint. The color of the peduncle is greener than, but closest to 137A.

REPRODUCTIVE ORGANS

Stamens: Anthers and filaments are minute and not clearly visible.

Pollen: RHS 155 D, produced abundantly.

Pistil: White in color, conical protruding between the staminate flowers, firmly fixed to the main axil. The pistillate flowers extend approximately 3 mm beyond the staminate flowers.

OTHER OBSERVATIONS

Pest And Disease Resistance/Susceptibility: Preventive disease and pest control measures used to grow crops of 'Connie' are typical of ordinary commercial practice. 'Connie' has no particular sensitivity to common pests or pathogens. By comparison, 'Connie' is more resistant to disease than its parents, 'Petite' and 'Linda'. Otherwise, 'Connie' is similar to 'Viscount' in disease resistance.

Seeds: 'Connie' has been used as a plant in hybridization. The plant produces viable pollen and seeds. The seeds are approximately 2 mm in length, reniform in shape, and light to medium brown in color. Surface texture of the seed coat is pitted. Each individual capsule contains approximately 1 to 6 seeds. Depending on size and degree of pollination, a single inflorescence can yield 500 or more seeds.

We claim:

1. A new and distinct cultivar of Spathiphyllum plant named 'Connie', as illustrated and described.

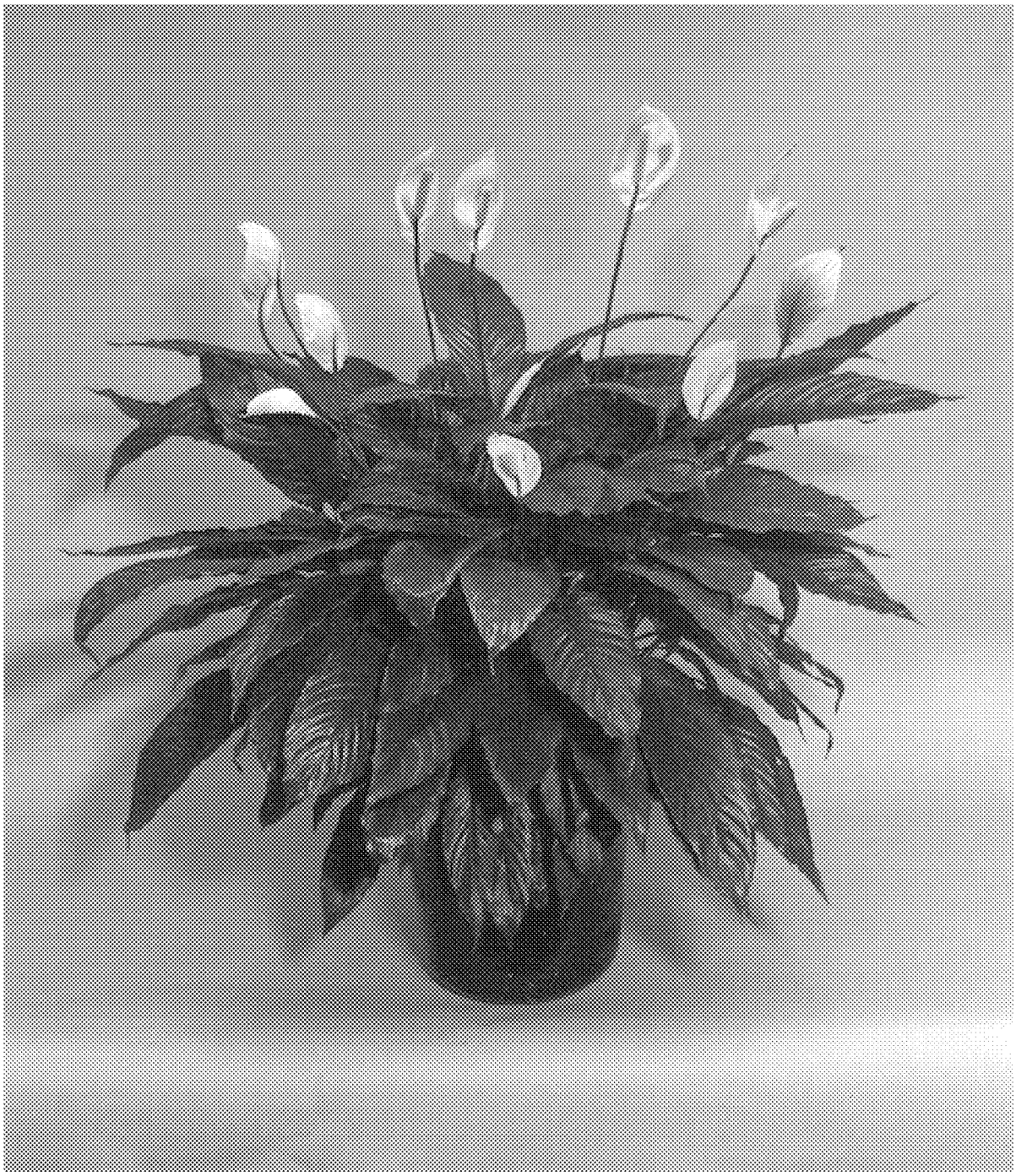

* * * * *